US012690762B2

(12) United States Patent
Sharma

(10) Patent No.: US 12,690,762 B2
(45) Date of Patent: Jul. 28, 2026

(54) OVER THE SCOPE CLIP

(71) Applicant: BOSTON SCIENTIFIC MEDICAL DEVICE LIMITED, Galway (IE)

(72) Inventor: Deepak Kumar Sharma, Muzaffarnagar (IN)

(73) Assignee: Boston Scientific Medical Device Limited, Galway (IE)

( * ) Notice: Subject to any disclaimer, the term of this patent is extended or adjusted under 35 U.S.C. 154(b) by 213 days.

(21) Appl. No.: 18/753,665

(22) Filed: Jun. 25, 2024

(65) Prior Publication Data

US 2025/0057408 A1 Feb. 20, 2025

Related U.S. Application Data

(60) Provisional application No. 63/520,278, filed on Aug. 17, 2023.

(51) Int. Cl.
| | |
|---|---|
| *A61B 17/122* | (2006.01) |
| *A61B 1/273* | (2006.01) |
| *A61B 17/128* | (2006.01) |

(52) U.S. Cl.
CPC ............ *A61B 1/273* (2013.01); *A61B 17/122* (2013.01)

(58) Field of Classification Search
CPC ..... A61B 17/083; A61B 17/10; A61B 17/122; A61B 17/1227; A61B 17/128; A61B 17/1285; A61B 17/0057; A61B 17/068; A61B 17/0686; A61B 17/064; A61B 17/0644; A61B 2017/00296; A61B 1/273
See application file for complete search history.

(56) References Cited

U.S. PATENT DOCUMENTS

| | | | | |
|---|---|---|---|---|
| 6,197,042 B1 * | 3/2001 | Ginn | ................... | A61B 17/128 |
| | | | | 606/139 |
| 2011/0208210 A1 * | 8/2011 | Baur | ...................... | A61B 18/14 |
| | | | | 606/142 |
| 2020/0397445 A1 * | 12/2020 | Shikhman | .......... | A61B 17/1227 |
| 2022/0133323 A1 * | 5/2022 | Evers | .................... | A61B 34/71 |
| | | | | 606/139 |
| 2022/0378432 A1 | 12/2022 | Sharma et al. | | |
| 2023/0225740 A1 | 7/2023 | Sharma | | |

* cited by examiner

*Primary Examiner* — Kathleen S Holwerda
(74) *Attorney, Agent, or Firm* — Fay Kaplun & Marcin, LLP

(57) ABSTRACT

A clipping system for treating tissue includes an adapter, a clip, an extending member, and a control wire. The adapter is mounted over an insertion device. The clip is mounted over the adapter and includes a connecting member connecting to first and second jaws. The jaws are configured to move between an insertion configuration and an initial deployed configuration. The extending member is coupled to the clip and the adapter and extends to abut the connecting member. The control wire is received within the extending member to move the clip between the insertion configuration, the initial deployed configuration and a review configuration. The control wire connects to the clip via a releasable link to retract the clip proximally over the adapter to force the clip to open. The releasable link is configured to release when the control wire is subject to a force exceeding a predetermined threshold value.

15 Claims, 18 Drawing Sheets

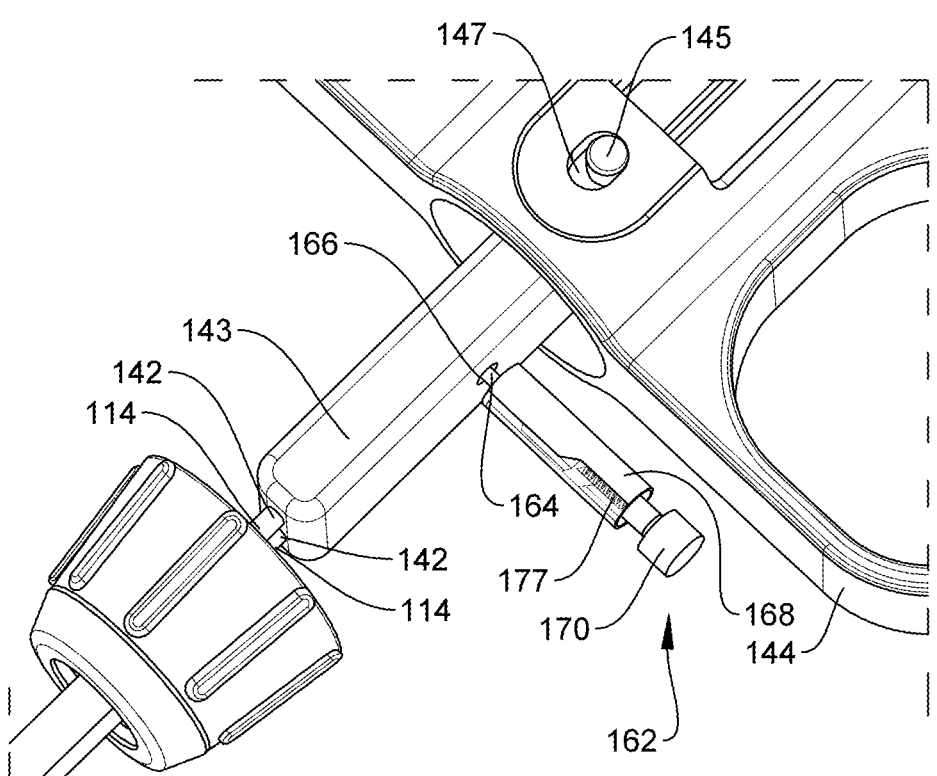
FIG. 5
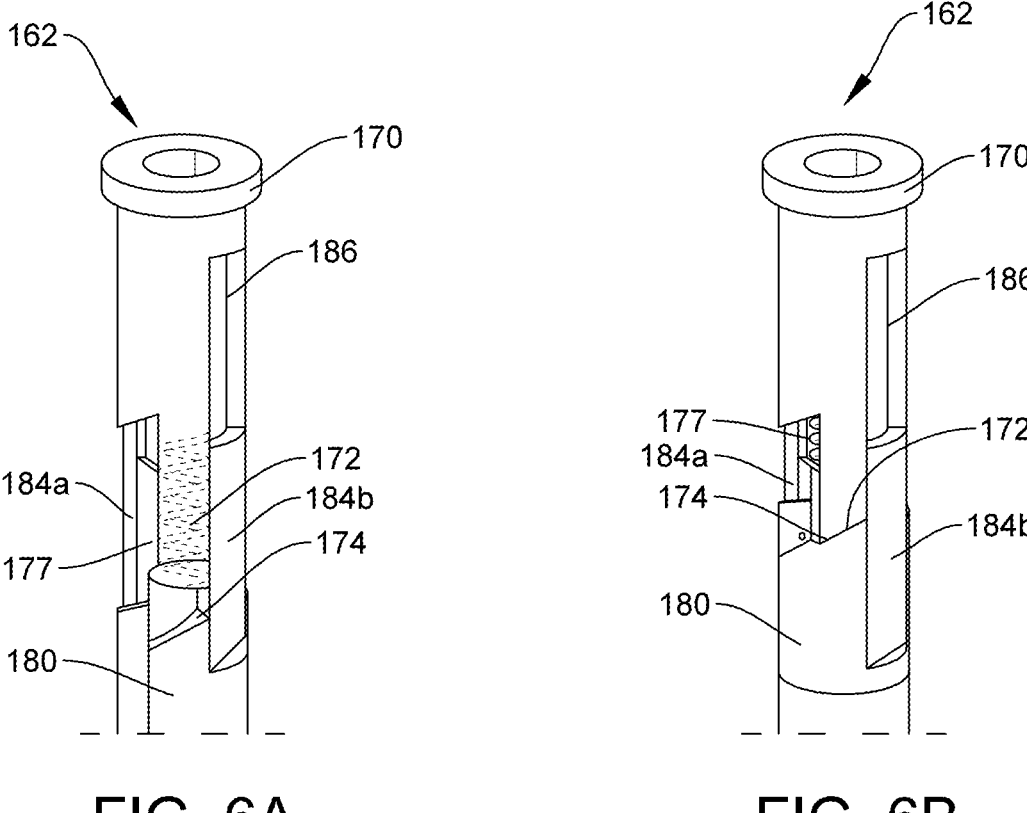
FIG. 6A FIG. 6B

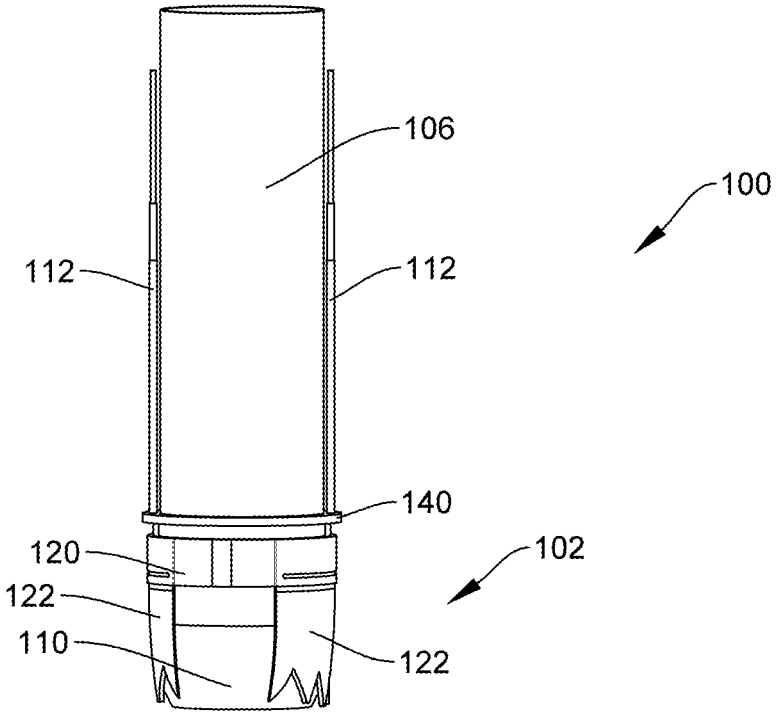
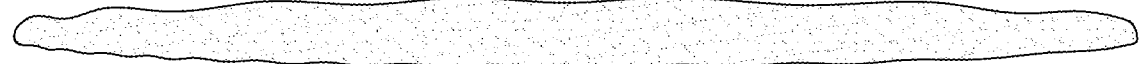
FIG. 14A

OVER THE SCOPE CLIP

PRIORITY CLAIM

The present disclosure claims priority to U.S. Provisional Patent Application Ser. No. 63/520,278 filed Aug. 17, 2023; the disclosure of which is incorporated herewith by reference.

FIELD present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks). Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient.

In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed. Once deployed, if the clip is not in the desired position, such current over-the scope clips are generally incapable of being repositioned.

SUMMARY

The present disclosure relates to a clipping system for treating tissue. The system includes an adapter including a proximal portion configured to be mounted over a distal end of an insertion device and a distal portion extending distally from the proximal portion. The system also includes a clip configured to be mounted over the distal portion of the adapter. The clip includes a connecting member connecting to first and second jaws configured to move between an insertion configuration, in which the first and second jaws extend about opposing portions of the distal portion of the adapter and are separated from one another to receive the tissue therebetween, and an initial deployed configuration, in which the clip is moved distally off of the adapter so that the first and second jaws are drawn toward one another to grip the tissue therebetween.

In addition, the system includes a first extending member releasably coupled to the clip and movably connected to the adapter. The first extending member includes a distal end extendable to abut against the connecting member. Furthermore, the system includes a first control wire slidably received within the first extending member so that movement of the first control wire relative to the first extending member moves the clip between the insertion configuration, the initial deployed configuration and a review configuration in which the adapter is withdrawn proximally away from the clip while the first control wire remains coupled to the clip to enhance visual observation of the clip. The first control wire is operable to retract the clip proximally over the adapter so that the clip is forced open as the clip is retracted over the adapter, a first releasable link connecting the first control wire to the clip, the first releasable link being configured to release when the first control wire is subject to a force exceeding a predetermined threshold value.

In an embodiment, the system further includes a second extending member releasably
coupled to the clip and movably connected to the adapter, the second extending member including a distal end received within the connecting member; and a second control wire slidably received within the second extending member, the second control wire being operable in conjunction with the first control wire to retract the clip proximally over the adapter so that the clip is forced open as the clip is retracted over the adapter, a second releasable link connecting the second control wire to the clip. The second releasable link is configured to release when the second control wire is subject to a force exceeding the predetermined threshold value.

In an embodiment, the system further includes a first flexible member slidably receiving the first extending member therein, the first flexible member extending from a proximal end that, in use, remains outside a body accessible to a user, to a distal end coupled to the adapter.

In an embodiment, the first jaw includes a proximal end received within a first space in the connecting member, the first jaw including a substantially tubular proximal portion and a distal portion curving toward a distal end at a longitudinal axis of the connecting member.

In an embodiment, the first control wire includes an enlarged distal end received within a first socket of the connecting member.

In an embodiment, the enlarged distal end of the first control wire is coupled to a proximal portion of the first control wire via a first link configured to separate when a force exerted on the first control wire exceeds a predetermined threshold level.

In an embodiment, the first socket is configured so that, when the first link separates, the enlarged distal end of the first control wire is retained within the first socket.

In an embodiment, the second jaw includes a proximal end received within a second space in the connecting member, the second jaw including a substantially tubular proximal portion and a distal portion curving toward a distal end configured to meet the distal end of the first jaw at the longitudinal axis of the connecting member.

In an embodiment, the first jaw includes a tab at a proximal end thereof and wherein the connecting member includes a slot configured to receive the tab when the first jaw is moved distally through the connecting member to a locking position to lock the first jaw in position on the connecting member.

In an embodiment, adapter includes a tapered distal end configured to slidably engage an inner surface of the first jaw as the first jaw is moved proximally over the adapter.

In addition, the present disclosure relates to a clipping system for treating tissue which includes an endoscope extending longitudinally from a proximal end to a distal end. The system also includes an adapter having a proximal portion configured to be mounted over a distal end of an insertion device and a distal portion extending distally from the proximal portion.

In addition, the system includes a clip configured to be mounted over the distal portion of the adapter. The clip includes a connecting member connecting to first and second jaws configured to move between an insertion configuration, in which the first and second jaws extend about opposing portions of the distal portion of the adapter and are separated from one another to receive the tissue therebetween, and an initial deployed configuration, in which the clip is moved distally off of the adapter so that the first and second jaws are drawn toward one another to grip the tissue therebetween.

Furthermore, the system includes first and second extending members releasably coupled to the clip and movably connected to the adapter, each of the first and second extending members including a distal end abutting the connecting member.

In addition, the system includes first and second control wires each of which is slidably received within a corresponding one of the first and second extending members so that movement of the first and second control wires relative to the first and second extending members moves the clip between the insertion configuration, the initial deployed configuration and a review configuration in which the adapter is withdrawn proximally away from the clip while the first and second control wires remain coupled to the clip, the first and second control wires being operable to retract the clip proximally over the adapter so that the clip is forced open as the clip is retracted over the adapter, each of the first and second control wires being coupled to the connecting member via a releasable link configured to release when the first and second control wires are subject to a force exceeding a predetermined threshold value.

In an embodiment, the system further includes a handle; a first actuator; and a locking mechanism selectively locking the first and second extending members to the first actuator.

In an embodiment, the first actuator is a spool slidable relative to a body of the handle and wherein the handle further includes a second actuator coupled to the first and second control wires, the second actuator configured to move the first and second control wires proximally and distally within the respective ones of the first and second extending members.

In an embodiment, the adapter includes a tapered distal end configured to slidably engage an inner surface of the first jaw as the first jaw is moved proximally over the adapter.

In an embodiment, the locking mechanism includes a spring biased member selectively lockable in a first position in which the spring biased member contacts the first and second extending members to lock the first and second extending members in position relative to the spool and a second position in which the spring biased member is out of contact with the first and second extending members freeing the first and second extending members to move relative to the spool.

In addition, the present disclosure relates to a method for treating tissue. The method includes inserting to a target area in a body lumen, a clip mounted over an adapter, the clip including a connecting member slidably receiving therein first and second jaws, wherein the first and second jaws are maintained during insertion of the clip to the target area in an insertion configuration in which jaws of the clip are separated from one another by the adapter; drawing the tissue into a channel of the adapter and between the jaws of the clip; moving the clip distally off of the adapter to permit the clip to move from the insertion configuration to an initial deployed configuration by advancing distally first and second control wires releasably coupled to the clip, the jaws of the clip being biased toward the initial deployed configuration in which the jaws extend toward one another to grip the tissue drawn into the adapter, a distal end of each of the first and second control wires s being connected to a remaining length thereof via a releasable link; and drawing the adapter proximally away from the clip while the clip remains coupled to the first and second control wires to a review configuration.

In an embodiment, when it is determined that the clip requires repositioning, drawing the first and second control wires proximally relative to the adapter until the clip is drawn proximally over the adapter toward the insertion configuration to open the jaws to free the clip from the previously clipped tissue, further comprising, after the clip has been freed from the previously clipped tissue, repositioning the clip over the target tissue.

In an embodiment, the method further includes pushing first and second extending members slidably over the first and second control wires into the connecting member to push the first and second jaws through the connecting member until a locking structure at a proximal end of the first jaw engages a corresponding locking structure of the connecting member to lock the first jaw in a desired position relative to the connecting member.

In an embodiment, the locking structure of the first jaw is a tab and wherein the corresponding locking structure of the connecting member comprises a slot.

In an embodiment, each of the first and second control wires comprises an enlarged distal end received in a corresponding socket of the connecting member.

BRIEF DESCRIPTION

FIG. 5 shows a perspective view of a distal portion of the handle of the system of FIG. 1 showing the locking mechanism of FIG. 4.

FIG. 6A shows a perspective view of an actuator of the locking mechanism of FIG. 4 in a locked configuration.

FIG. 6B shows a perspective view of an actuator of the locking mechanism of FIG. 4 in an unlocked configuration.

FIG. 14A shows a perspective view of the distal portion of the system of FIG. 1 in a preliminary stage at which the device is positioned adjacent to target tissue to be captured.

DETAILED DESCRIPTION

Figure 1:
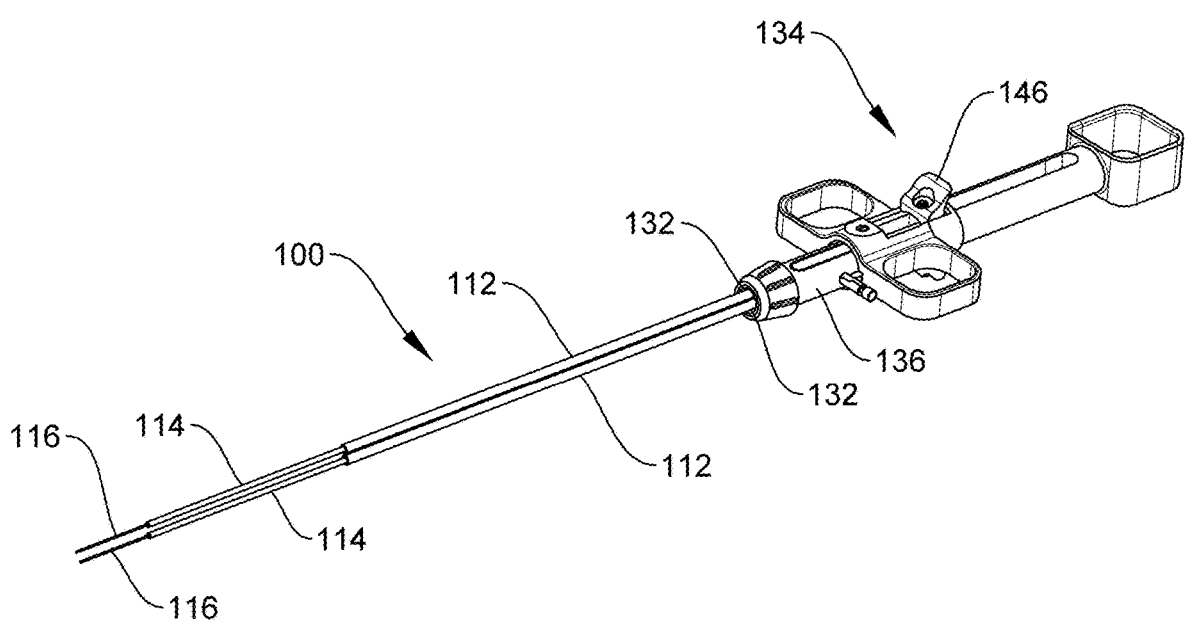
FIG. 1 shows a perspective view of a proximal portion of a clipping system according to an exemplary embodiment of the present disclosure.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a final deployment thereof. Exemplary embodiments of the present disclosure comprise a clip mountable over an adapter coupled to a distal end of an endoscope and releasably coupled to extending members so that the clip may be moved relative to the adapter between an insertion configuration, an initial deployed configuration, and a review configuration, in which the clip can be viewed via the endoscopic viewing system prior to being finally deployed.

According to an exemplary embodiment, a distal end of a control wire in each of the extending members is coupled to a proximal ring of the clip. Each control wire includes a frangible link between the distal end and a remaining length thereof that is configured to break, fail or otherwise separate when subject to a force exceeding a predetermined threshold force so that, during a final deployment of the clip, the frangible link breaks or separates to release the clip from control wires and the extending members.

In an exemplary embodiment, the distal ends of the control wires are coupled to the clip so that, upon breaking or separating of the frangible link, the distal ends of the control wires remain attached to the clip, preventing any shed parts during the final deployment, while the remaining lengths may be removed from the body. As will be understood by those of skill in the art, some current clip designs create shed parts during the deployment process of separating the clip from the catheter so that shed parts are left to pass through the GI tract naturally. As larger defect cases become more prevalent, some physicians may prefer clips that do not generate shed parts to eliminate the possibility of shed parts becoming closed in the defects.

While the control wires remain coupled to the clip—e.g., the frangible link remains intact since a force applied thereon does not exceed the predetermined threshold value-the control wires may be moved longitudinally relative to the endoscope to move the clip between an insertion configuration, an initial deployed configuration and a review configuration. In the insertion configuration, the clip is mounted over the adapter in a proximal position maintained in the insertion configuration ready to receive tissue between jaws thereof while the clip's position minimizes its occlusion of the field of view of the endoscopic vision system. The insertion configuration is configured to facilitate insertion of the endoscope to a target site adjacent to tissue to be clipped while the system allows the clip to be deployed and clipped over tissue in an initial deployed configuration. The device permits the endoscope and the adapter to be withdrawn proximally away from the clip and the tissue over which it is clipped while the clip remains coupled to the device in a review configuration.

As the endoscope and the adapter are withdrawn proximally while the clip remains in place over the target tissue, the field of view of the vision system of the endoscope widens to show the clip and the tissue clipped thereby so that the operator can determine whether the position of the clip is desirable or in need of adjustment. If the operator determines that the clip is positioned as desired, the clip is deployed by releasing the clip from the control wires/extending members and left in place clipped over the target tissue. If the operator determines that the position of the clip needs adjustment, the endoscope and adapter are moved distally to a position adjacent to the clip. The clip is then drawn proximally over the adapter to reopen the clip which is drawn proximally over the adapter forcing the clip to open against its natural bias as the clip slides proximally back over the adapter to return to the insertion configuration.

After the clip has been removed from the tissue and returned to the insertion configuration, the operator can re-position the endoscope as desired, draw a new portion of target tissue into the adapter (e.g., under suction or a grasper applied via a working channel of the endoscope) and once more deploy the clip from the adapter over the target tissue in the initial deployed position. The endoscope is then withdrawn proximally once again as the clip remains coupled to the device so that the device moves again into the review configuration.

The position of the clip and the clipped tissue are again observed and, this process may be repeated until the operator determines that the clip is positioned as desired. When the operator sees that the tissue over which the clip is closed is the desired portion of tissue, the frangible links of the control wires may be broken to release the clip therefrom, so that the clip moves to the final deployed configuration in which it is fully separated from the rest of the system and the endoscope. It will be understood by those of skill in the art that terms proximal and distal, as used herein, are intended to refer to a direction toward and away from, respectively, a user of the device.

As shown in FIGS. 1-14, a clipping system 100 for treating tissue defects and/or perforations according to an exemplary embodiment comprises a clip 102 configured to be inserted through, for example, a body lumen to a target area to clip a target tissue thereof. The clip 102 is insertable to the target area via an insertion device 104 including, for example, an endoscope 106. As shown in FIGS. 1-4, the clip 102 is coupled to a distal end 108 of the endoscope 106 via an adapter 110, which is mounted over the distal end 108 of the endoscope 106.

The adapter 110 of this embodiment is sized and shaped to closely match a profile of the endoscope and is hollow to define a central channel therein that is open, for example, a working channel and a vision system of the endoscope (e.g., which terminate in a distal face of the endoscope as would be understood by those skilled in the art). The clip 102 is configured to be moved relative to the adapter 110 and the endoscope 106 via flexible members 112 each of which house therein a tube 114 with a control wire 116 slidably received within each of the tubes 114. The clip 102 is releasably coupled to the control wires 116. The clip 102 is movable from an insertion configuration to an initial deployed configuration and from the initial deployed configuration to a review configuration by moving the tubes 114 within the flexible members 112 as will be described in more detail below.

If the user desires, the clip 102 may be moved from the review configuration back to the insertion configuration and then moved again to the initial deployed configuration in a new position. When the user is satisfied that the clip 102 has been positioned as desired, the clip 102 may be moved from the initial deployed configuration to a final deployed configuration in which the clip 102 is separated from the control wires 116 and the rest of the system 100 so that the clip 102 may be left in place clipped over desired tissue while the rest of the system 100 is withdrawn from the body.

Figures 9, 10:
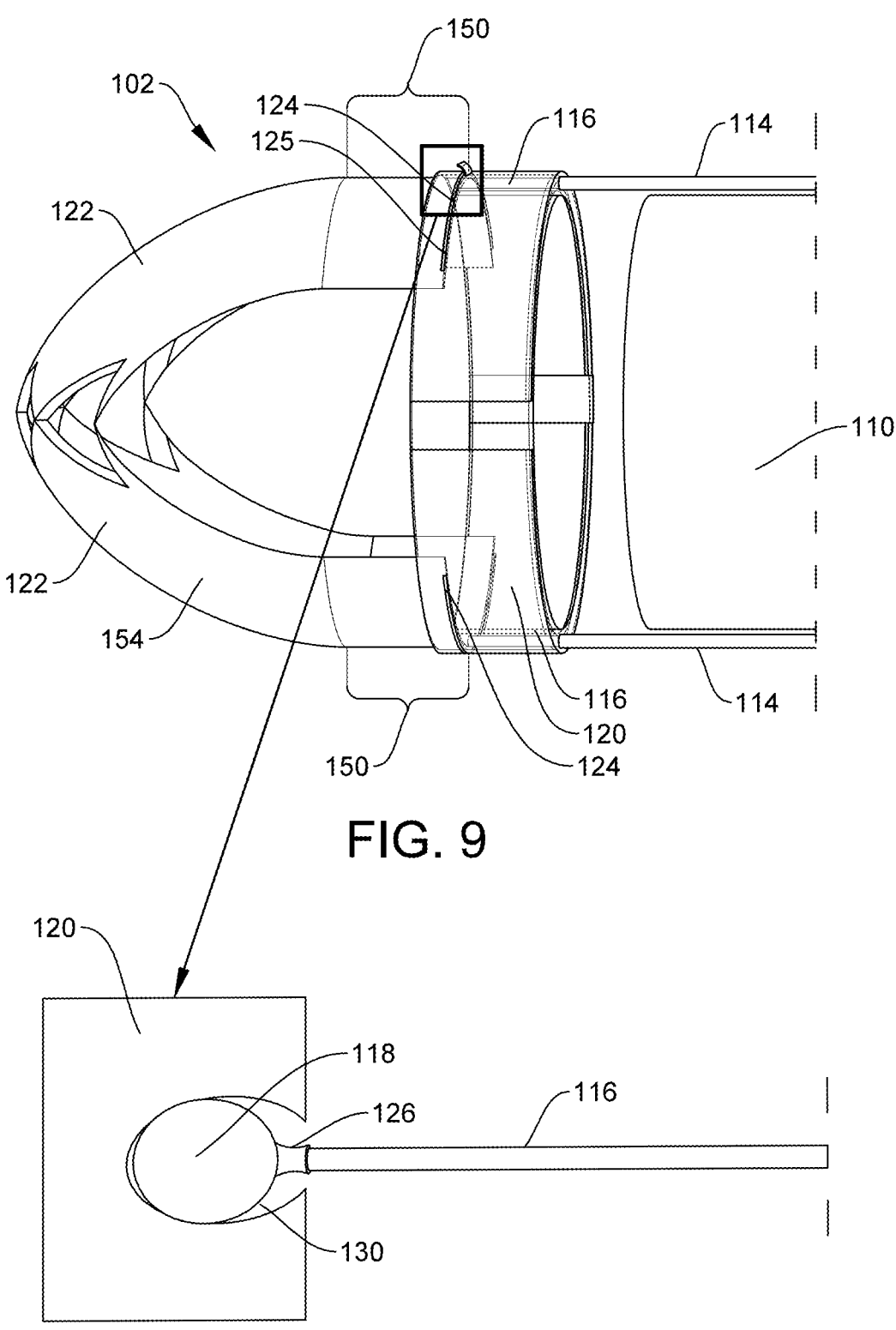
FIG. 9 shows a transparent perspective view of the distal end of the system of FIG. 1 with the clip in a review configuration.
FIG. 10 shows a cross-sectional view of a connection between a control wire of the system of FIG. 1 and the clip.
Figure 11:
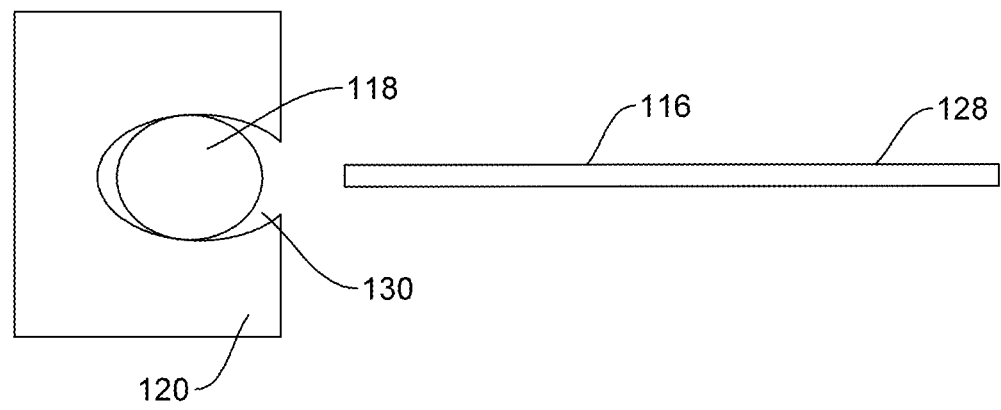
FIG. 11 shows a cross-sectional view of the connection between a control wire of the system of FIG. 10 after separation of the control wire from the clip.
Figure 12:
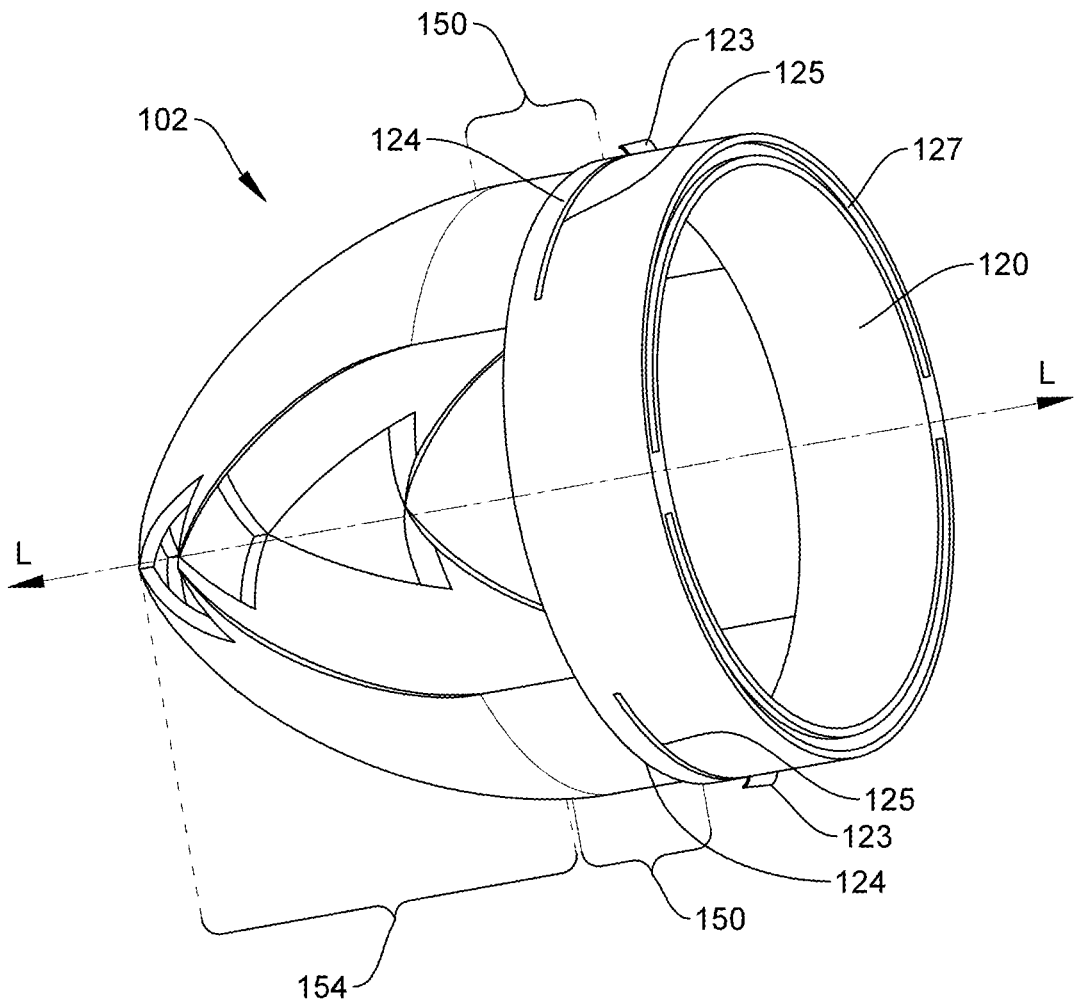
FIG. 12 shows a perspective view of the clip of the system of FIG. 1 after being deployed.
Figure 13:
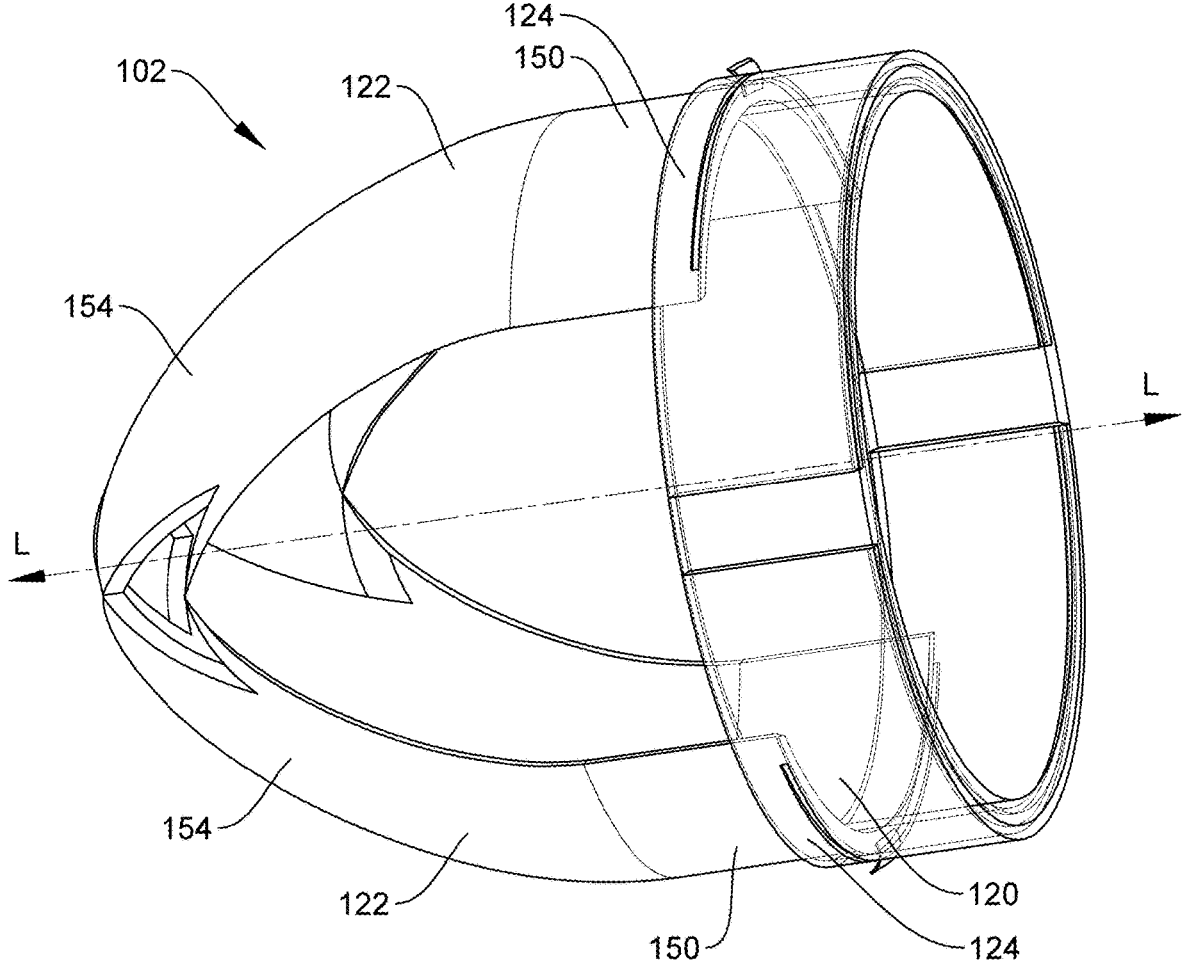
FIG. 13 shows a partially transparent perspective view of the clip of FIG. 12.

As shown in FIGS. 10 and 11, each of the control wires 116 includes an enlarged distal end 118 coupled to a connecting ring 120 of the clip 102. The connecting ring 120 of the clip 102 slidably receives the proximal end 124 of each of a plurality of jaws 122. In this embodiment, the clip 102 includes two jaws 122 although, as would be understood by those skilled in the art, any desired number of jaws 122 may be included. Furthermore, as would be understood by those skilled in the art, a size and shape of a proximal portion 150 of each jaw 122 conforms to a shape and size of an opening in the connecting ring 120 within which the proximal portions 150 are received.

In this embodiment, the connecting ring 120 is substantially cylindrical as are the proximal portions 150 of the jaws 122. However, the shapes of these elements may vary to accommodate the shape of the distal portion of the insertion instrument, etc. Each control wire 116 includes a frangible link 126 connecting the enlarged distal end 118 to a remaining portion 128 of each of the control wires 116. The frangible link 126 is configured to break, fail, or otherwise separate when a force applied thereto exceeds a predetermined threshold value to release the clip 102 therefrom to the final deployed configuration. Each of the enlarged distal ends 118 is received in a corresponding socket 130 formed within one or both of the jaws 122 wherein the sockets 130 are configured to prevent the enlarged distal ends 118 from moving proximally out of the sockets 130.

However, those skilled in the art will understand that, alternatively, the control wires 116 may be formed without the frangible links 126 if sockets 130 are constructed to include proximal ends (i.e., the portions constricting a proximal opening of the socket 130 through which the control wires 116 extend) configured to yield when a proximally directed force is applied thereto via the control wires 116. In this case, the control wires 116 and the enlarged distal ends 118 would not separate from one another upon final deployment of the clip 102 but would be pulled intact out of the sockets 130.

Each of the flexible members 112 is configured to be extended along a length of the endoscope from a proximal end 132 coupled to a body 136 of a handle 134 to a distal end 138 that is coupled to a flange 140 of the adapter 110 which in this embodiment is transparent to minimize occlusion of the field of view of the endoscopic vision system. While the frangible link 126 remains intact, longitudinal movements of the tubes 114 relative to the endoscope 106 move the clip 102 between the insertion configuration, the initial deployed configuration, and the review configuration. As would be understood by those skilled in the art, if the tubes 114 are held stationary while the control wires 116 are advanced distally, the jaws 122 will move distally relative to the connecting ring 120 while, if the tubes 114 and the control wires 116 are moved distally together, the entire clip 102 including the connecting ring 120 and the jaws 122 will move distally together.

Specifically, each of the tubes 114 extends from a proximal end 142 selectively coupled to a tube holder 143 via a locking mechanism 162. The tube holder 143 is coupled to the spool 144 of the handle 134 via a pin 145 of the tube holder 143 that is received within a slot 147 of the spool 144. Each of the tubes 114 extends from its proximal end 142 to a distal end distal of the flange 140 that is received within a space 127 of the connecting ring 120. Thus, when the locking mechanism 162 is engaged, movement of the spool 144 distally relative to the body 136 of the handle 134 moves the tubes 114 distally through the flexible members 112 pushing the connecting ring 120 and the clip 102 distally over the adapter 110. This movement of the spool 144 while the locking mechanism 162 is engaged also moves the control wires 116 proximally and distally along with the tubes 114 as the control wires 116 are coupled to the slider 146 which is coupled to the spool 144.

Movement of the spool 144 relative to the body 136 of the handle 134 moves the tubes 114 proximally and distally relative to the body 136 while movement of the slider 146 relative to the body 136 moves the control wires 116 relative to the body 136. As would be understood by those skilled in the art, if the slider 146 is moved relative to the spool 144, the control wires 116 are moved proximally or distally relative to the tubes 114 within which they are slidably received. The jaws 122 of the clip 102 of this embodiment are biased toward a closed tissue gripping configuration in which distal ends of the jaws 122 are drawn together to grip any tissue received therebetween. Thus, when the user engages the locking mechanism 162 and advances the spool 144 distally relative to the body 136, the tubes 114 push the clip 102 distally until the jaws 122 move distally beyond a distal end of the adapter 110. The jaws 122 will then close under their natural bias and grip any tissue positioned therebetween.

Figure 2:
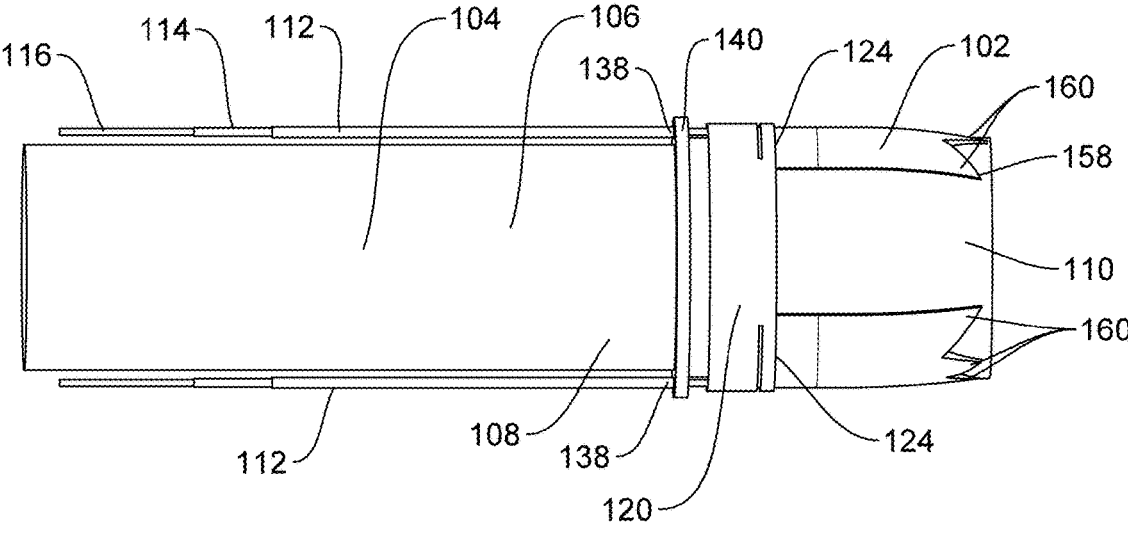
FIG. 2 shows a side view of the distal portion of the clipping system of FIG. 1, in an insertion configuration.
Figure 3:
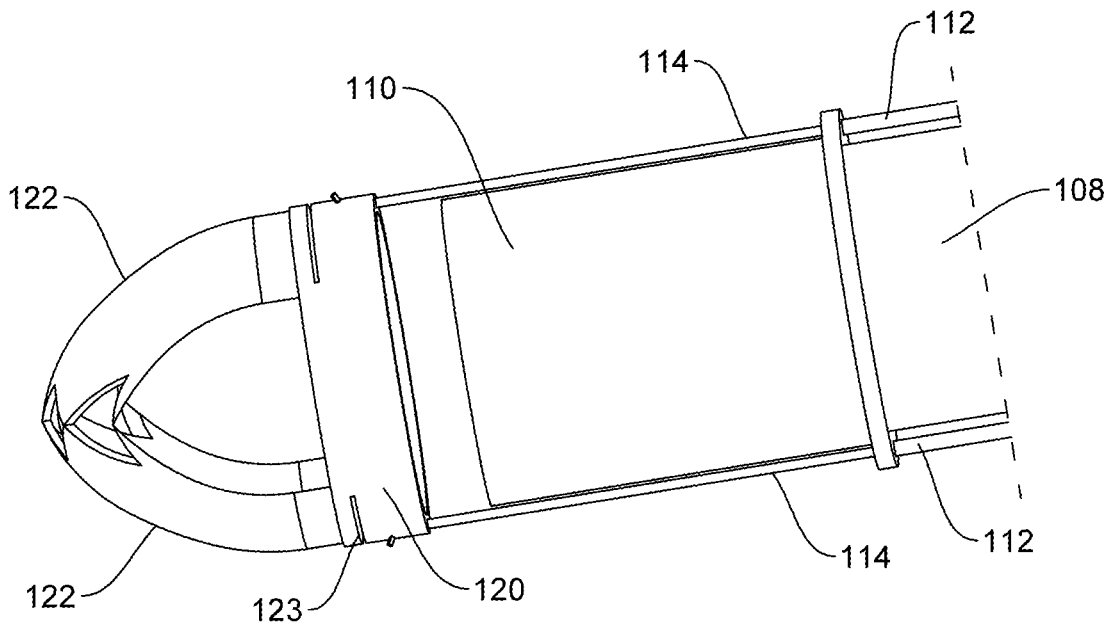
FIG. 3 shows a perspective view of the distal portion of the clipping system of FIG. 1, with the clip in a closed configuration.
Figure 4:
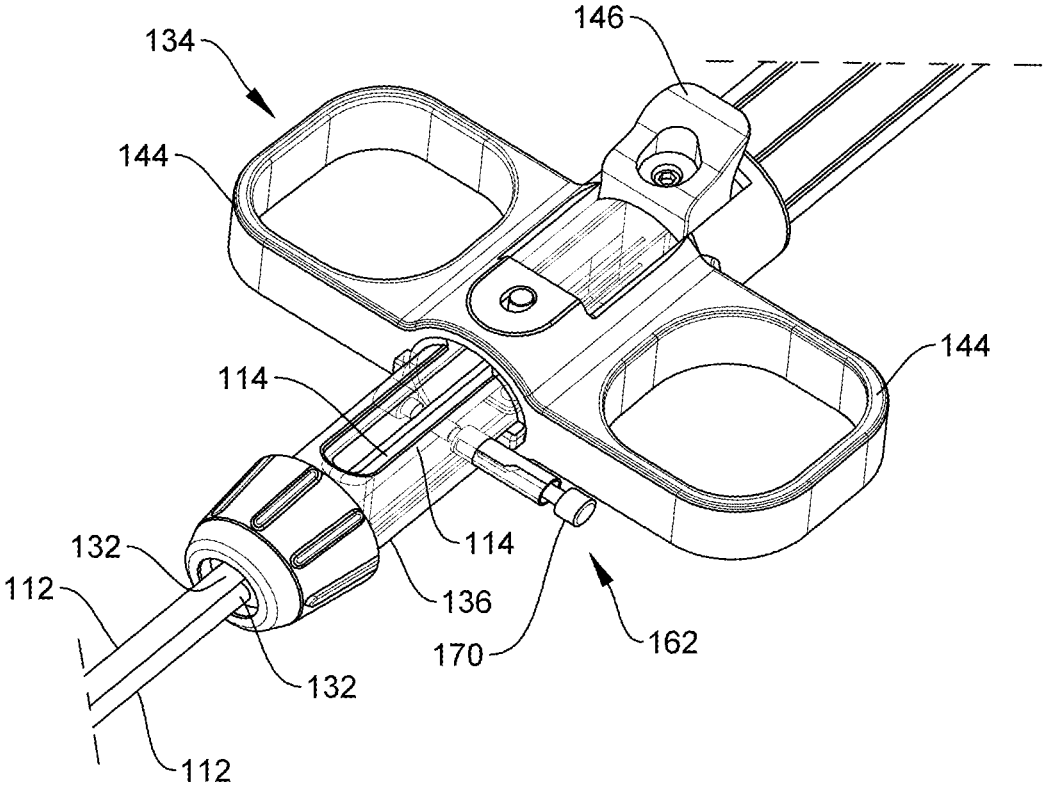
FIG. 4 shows a perspective view of a handle of the system of FIG. 1 showing a mechanism for locking a flexible coil in a desired position.
Figure 7:
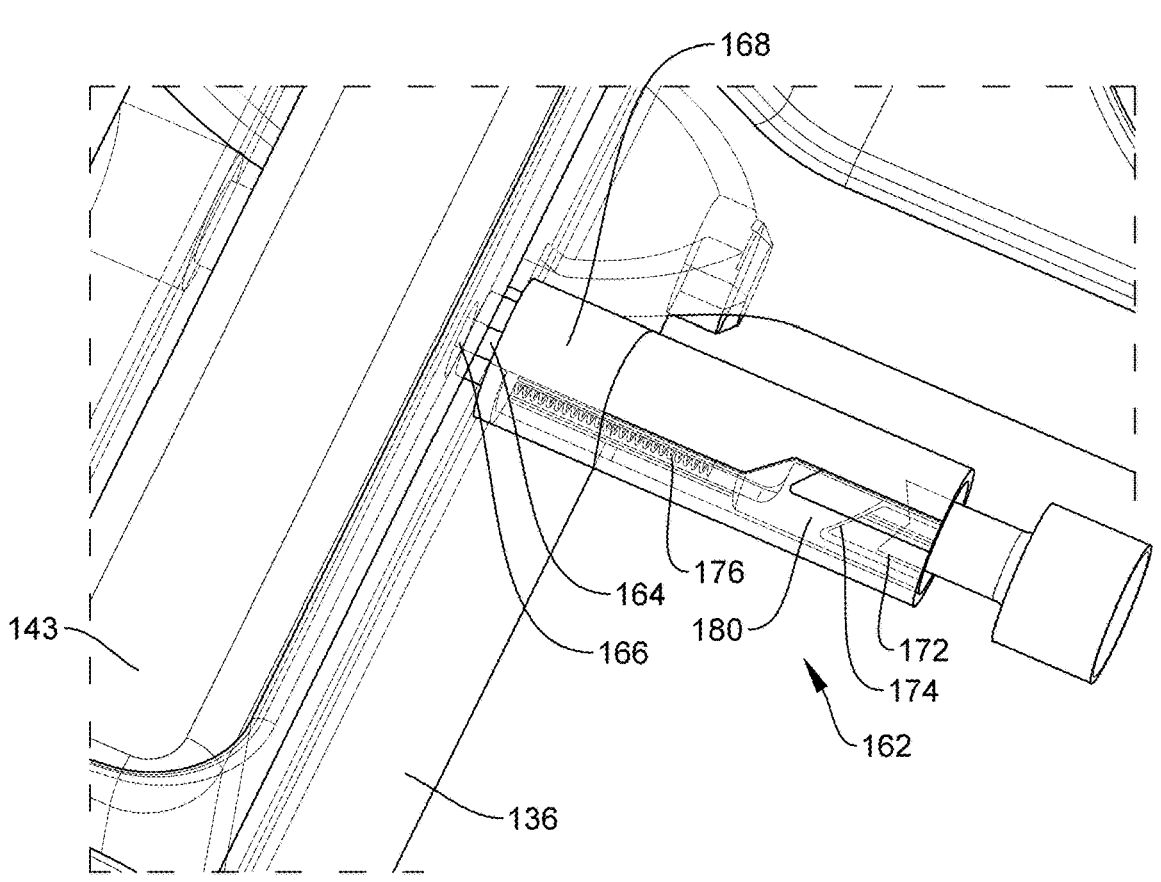
FIG. 7 shows a partially cross-sectional view of the locking mechanism of FIG. 4 with the actuator in a locked configuration.
Figure 8:
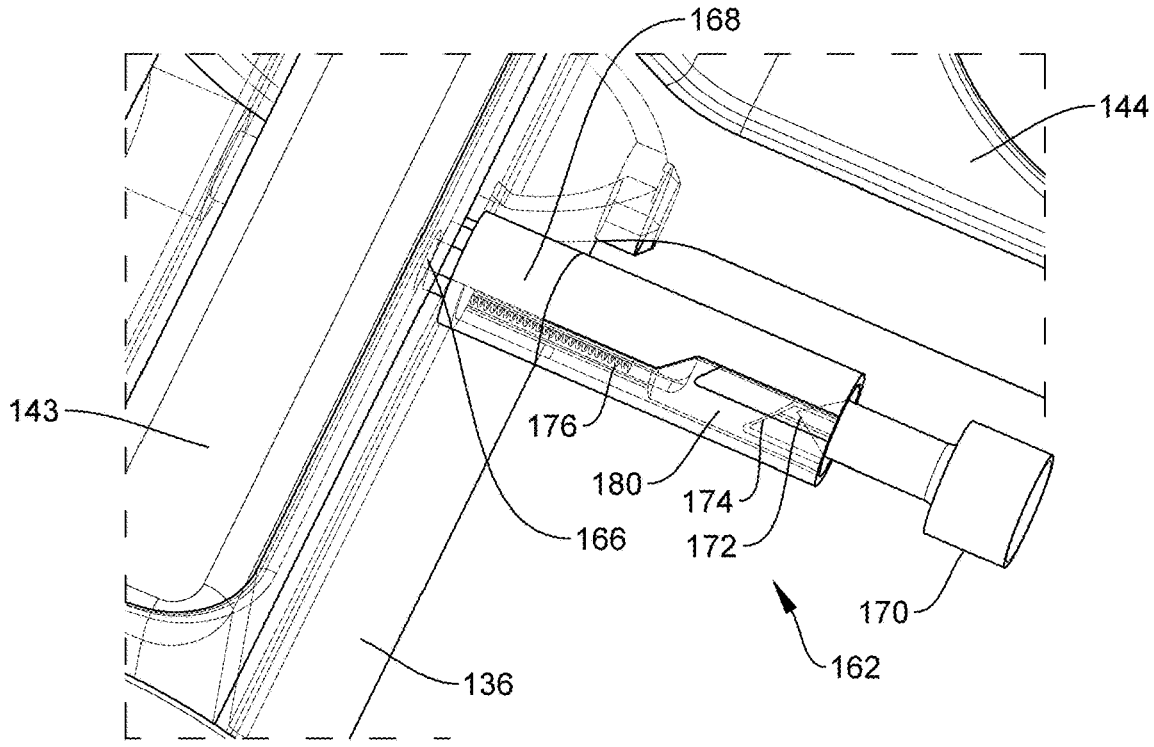
FIG. 8 shows a partially cross-sectional view of the locking mechanism of FIG. 4 with the actuator in an unlocked configuration.
Figure 14B:
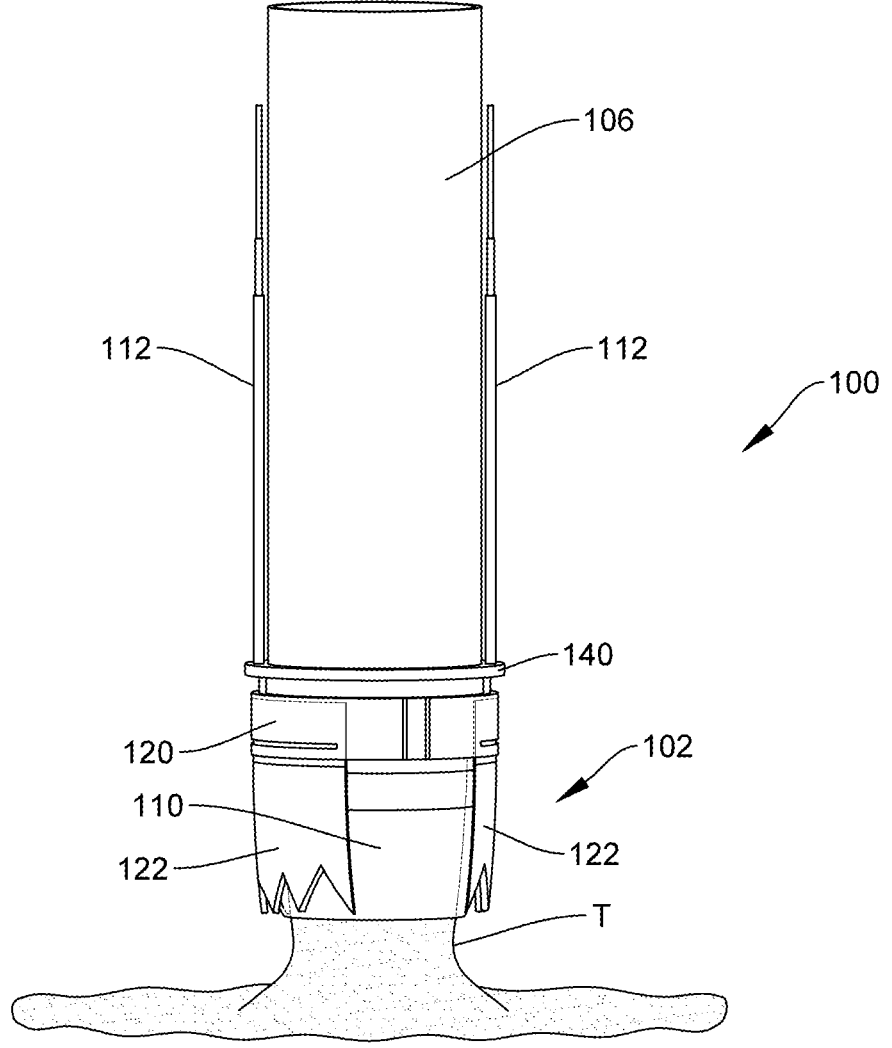
FIG. 14B shows a perspective view of the distal portion of the system of FIG. 1 in a preliminary stage at which target tissue is captured via suction.
Figure 14C:
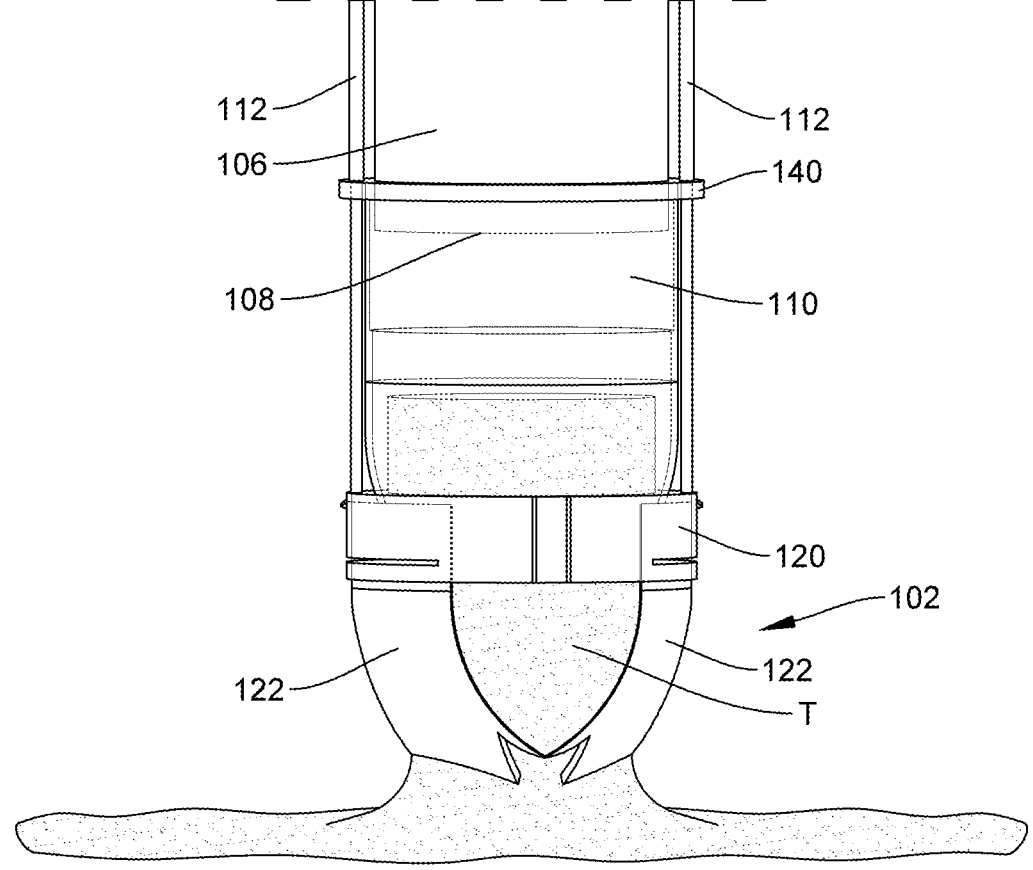
FIG. 14C shows a perspective view of the distal portion of the system of FIG. 1 in an initially deployed configuration.
Figure 14D:
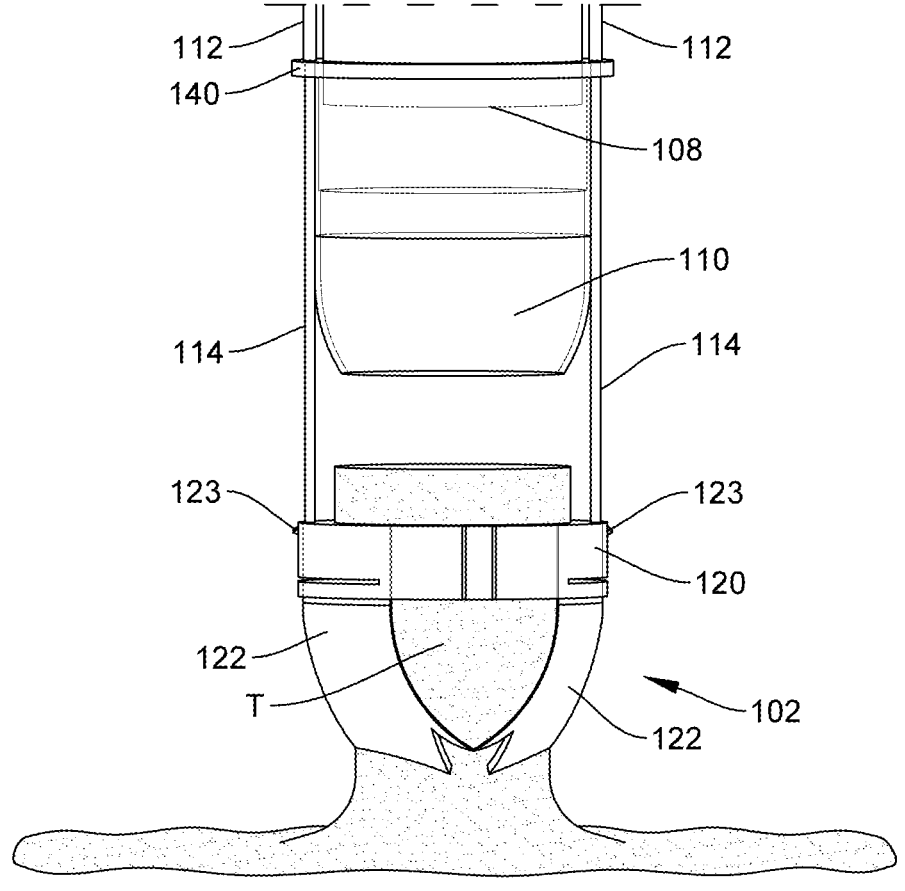
FIG. 14D shows a perspective view of the distal portion of the system of FIG. 1 in a review configuration.

As will be described in more detail below and as shown in FIGS. 14A and 14B, before the clip 102 is moved distally off the adapter 110 (i.e., with the clip 102 in the insertion configuration), the user may draw a target portion of tissue T into the channel of the adapter 110 (e.g., by applying suction or a grasper through a working channel of the endoscope 106). As shown in FIG. 2, in the insertion configuration, the clip 102 is mounted over the adapter 110 with jaws 122 separated from one another to receive tissue therebetween. To move the clip 102 from the insertion configuration to the initial deployed configuration (FIG. 14C), the tubes 114 are moved distally relative to the endoscope 106 (by operating the spool 144 as described above), moving the clip 102 distally until the jaws 122 project distally off the adapter 110 and close under their own bias (i.e., move to the an initial deployed configuration) to clip the tissue that has been drawn into the channel of the adapter 110.

After the jaws 122 have closed over this portion of tissue by moving the clip 102 to the initial deployed configuration (FIG. 14C), the clip 102 may be moved toward a review configuration (FIG. 14D) by extending the control wires 116 distally out of the tubes 114. Specifically, each of the control wires 116 extends from a proximal end coupled to a slider 146 that is slidably mounted on the spool 144 so that the slider 146 may be moved proximally and distally relative to both the body 136 and the spool 144 of the handle 134.

Thus, advancing the slider 146 distally relative to the spool 144 moves the control wires 116 distally out of the tubes 114 so that the enlarged distal ends 118 push the connecting ring 120 and the clip 102 distally away from the adapter 110 and the endoscope 106 while drawing the endoscope 106 proximally relative to the control wires 116 so that the clip 102 remains in place clipped over the tissue while the distal end of the endoscope 106 and the adapter 110 are spaced from the clip 102. In this configuration, the clip 102 remains tethered to the insertion device 104 via the control wires 116 while the field of view of the endoscope vision system relative to the clip 102 and the target tissue is widened while also allowing for movement of the endoscope 106 relative to the clip 102 to enable more extensive observation of the placement and/or position of the clip 102 relative to the target tissue.

Figure 14E:
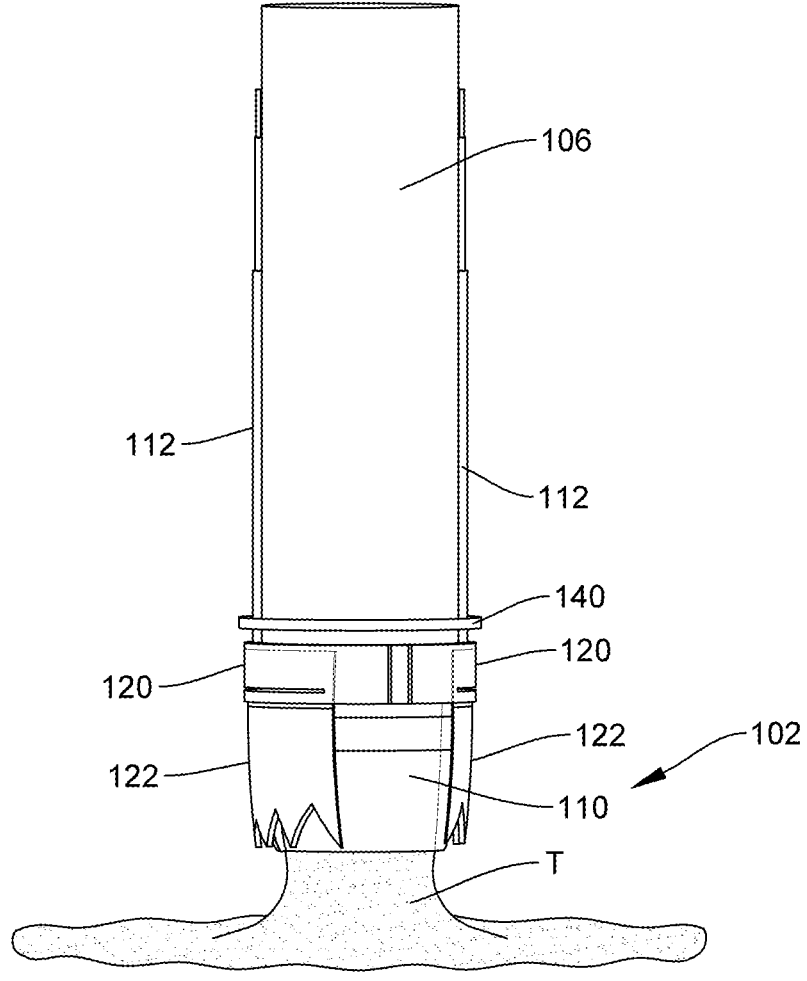
FIG. 14E shows a perspective view of the distal portion of the system of FIG. 1 with a clip that had previously been preliminarily deployed has been re-opened so that the clip can be repositioned.

As described below, if the user determines the position of the clip 102 is incorrect or sub-optimal, the user may move the endoscope 106 distally to a position adjacent to the clip 102 by sliding the endoscope 106 and the tubes 114 over the control wires 116 as the control wires 116 are withdrawn proximally (FIG. 14E). The endoscope 106 and the tubes 114 may be held in position immediately proximal of the clip as the clip 102 is retracted proximally over the distal end of the adapter 110. This forces the jaws 122 of the clip 102 open (FIG. 14E) releasing the previously clipped tissue (e.g., by, at the same time releasing any grasper or suction) and returns the clip 102 to the insertion configuration.

Figure 14F:
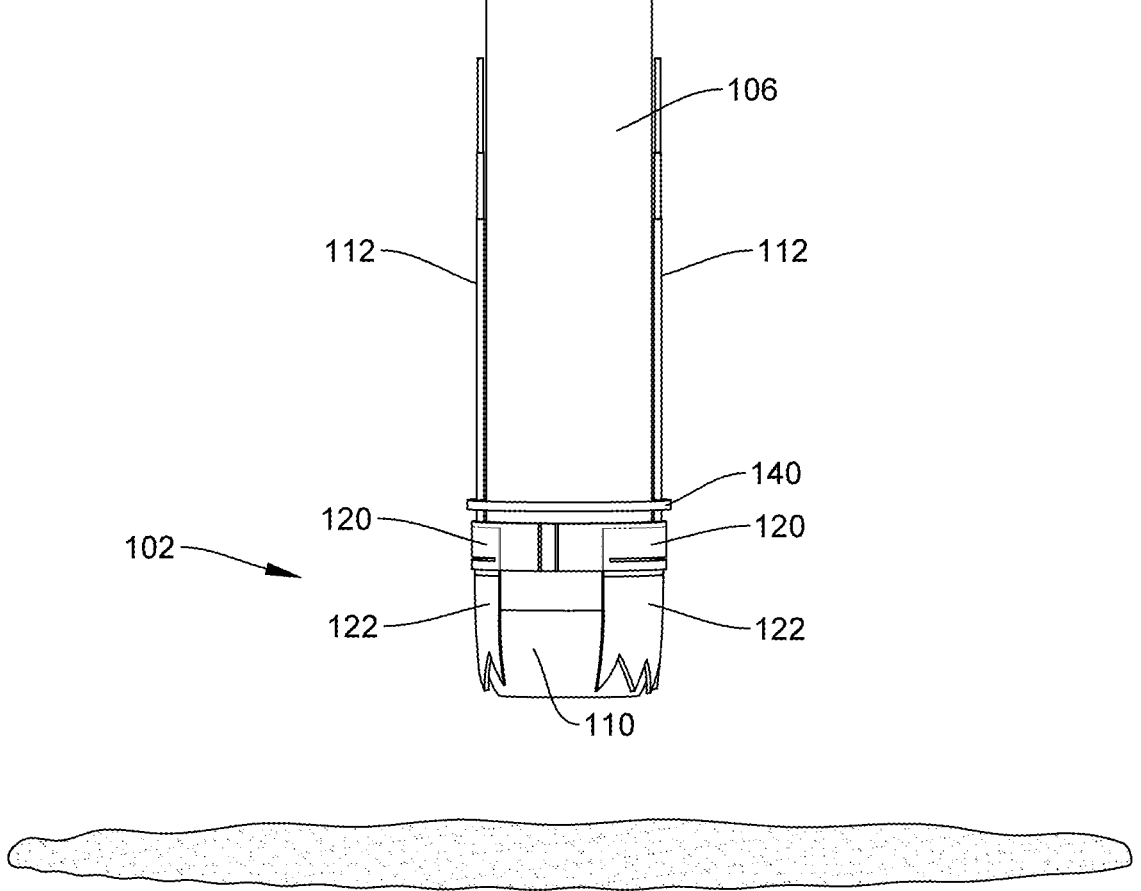
FIG. 14F shows a perspective view of the distal portion of the system of FIG. 1 with the device repositioned adjacent to a different portion of target tissue to be clipped.
Figure 14G:
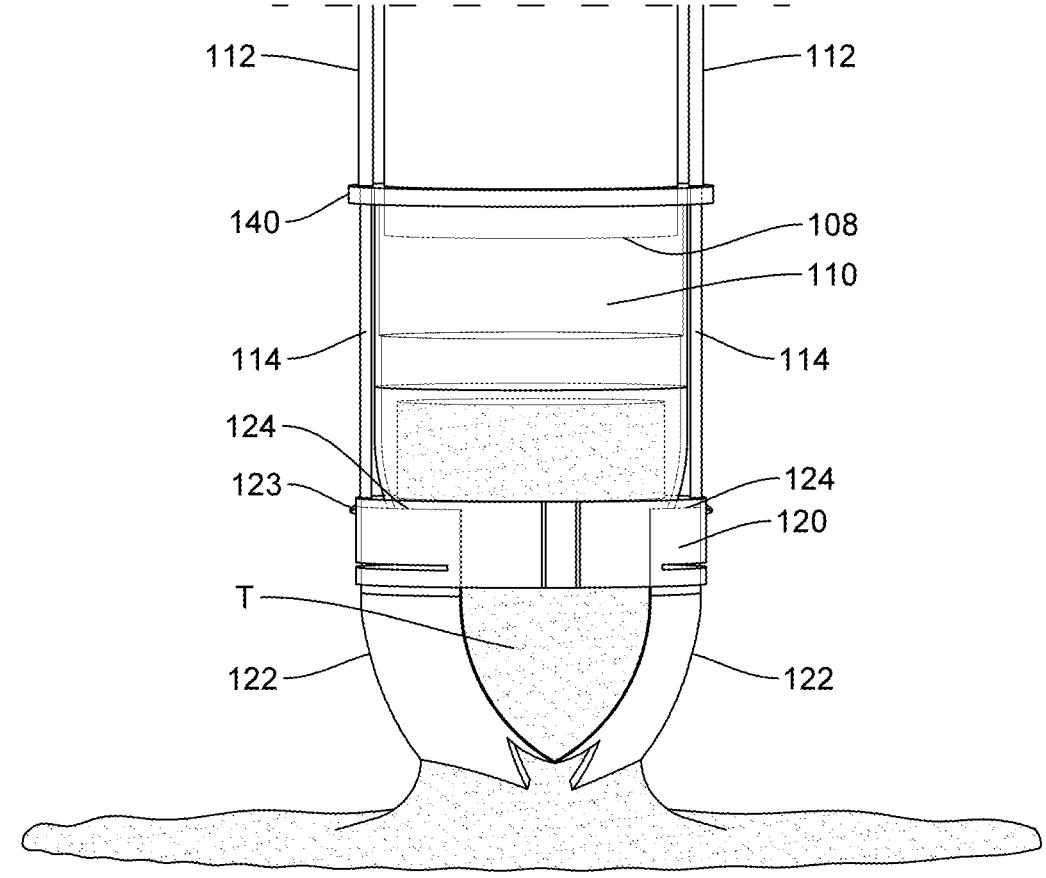
FIG. 14G shows a perspective view of the distal portion of the system of FIG. 1 with the clip initially deployed over the different portion of target tissue to be clipped.
Figure 14H:
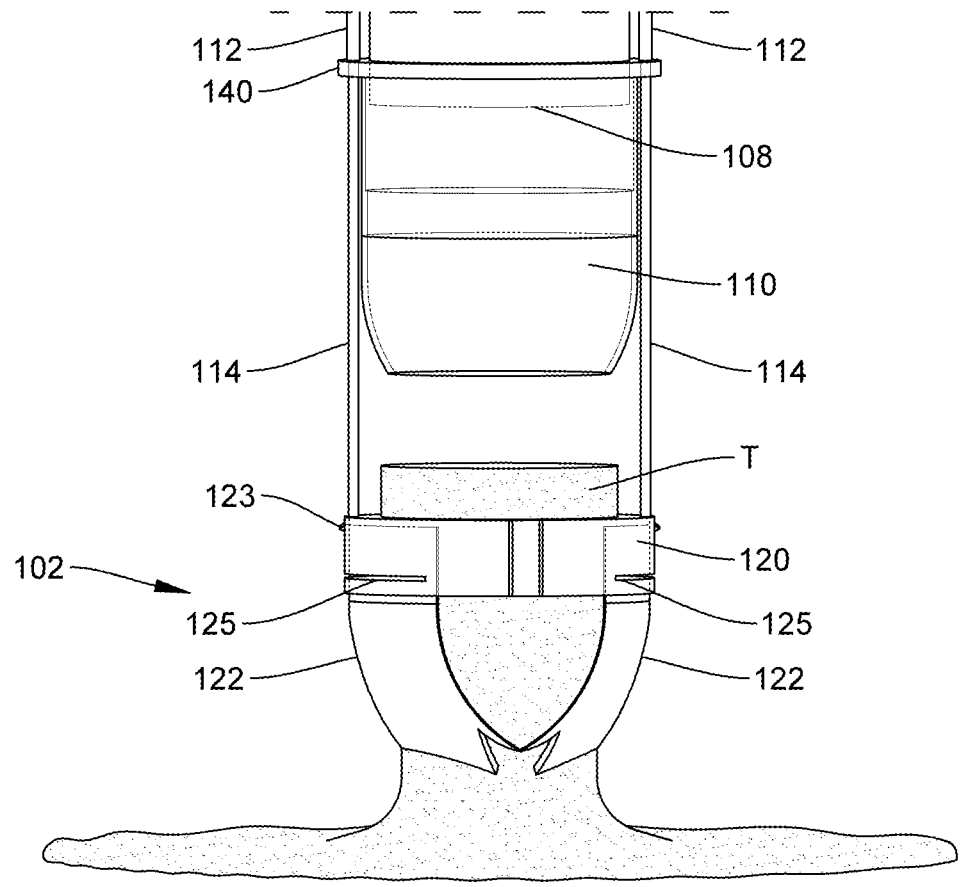
FIG. 14H shows a perspective view of the distal portion of the system of FIG. 1 with the clip clipped over the different portion of target tissue and the device withdrawn to the review configuration.
Figure 14I:
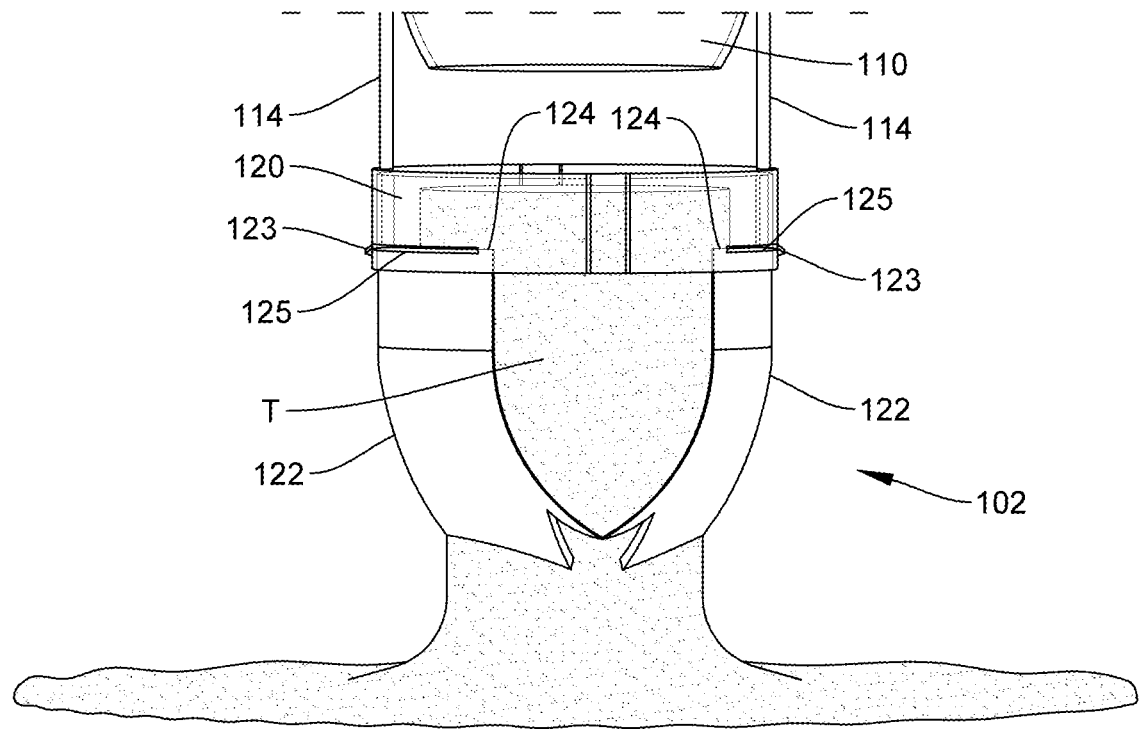
FIG. 14I shows a perspective view of the distal portion of the system of FIG. 1 with the jaws of the clip of FIG. 14H locked in position in a connecting ring.

The user may then reposition the endoscope 106 and the clip 102 and repeat these steps to adjust the placement and/or position of the clip 102 relative to a target tissue as desired, prior to a final deployment of the clip 102 (FIG. 14F). That is, if the operator determines in the review configuration that the clip 102 is not positioned as desired, the clip 102 may be reopened and removed from the tissue as many times as necessary so that the device can be repositioned until the clip 102 is closed over the desired portion of tissue (FIG. 14G).

When the user determines that the clip 102 has been positioned as desired and has been clipped over the target portion of tissue, the user locks the position of the tubes 114 relative to the spool 144 (i.e., by locking the tubes 114 with respect to the tube holder 143). Specifically, the locking mechanism 162 of this embodiment includes a pin 164 which, in a locking configuration, is extended into the tube holder 143 via a hole 166 in the tube holder 143 to press against and lock a position of the tubes 114 relative to the tube holder 143. In an unlocked configuration, the pin 164 is retracted into a body 168 of the locking mechanism 162 and withdrawn from the hole 166.

Thus, as the body 168 of the locking mechanism 162 is coupled to the body 136 of the handle 134, when the pin 164 is inserted into the hole 166 of the tube holder 143, the pin 164 engages the tubes 114 to lock them in place within the tube holder 143 which is coupled to the spool 144. When the pin 164 is withdrawn from the hole 166, the tubes 114 are free to move relative to the tube holder 143 and the spool 144. The locking mechanism 162 includes a spring actuator as will be described below. However, those skilled in the art will understand that any other suitable mechanism for selectively locking the position of the tube holder 143 relative to the body 136 of the handle 134 may be substituted for this mechanism if desired.

The spring actuator for locking mechanism 162 includes a push button 170 that extends to an angled cam surface 172 at its distal end. The cam surface 172 interfaces with a correspondingly angled cam surface 174 of a cam body 180 of the locking mechanism 162. The pin 164 extends from the distal end of the cam body 180 and a first spring 176 surrounds the pin 164 and abuts the distal end of the cam body 180 biasing the cam body 180 away from the hole 166 (e.g., toward the push button 170). The push button 170 is non-rotatably received within the body 168 while the cam body 180 is rotatably received therein.

The cam body 180 receives first and second stop members 184a, 184b fixed to the body 168 in slots 186 thereof so that, when the first and second stop members 184a, 184b are received within the slots 186, the cam body 180 is prevented from rotating within the body 168. The locking mechanism 162 includes a second spring 177 that is fixed around the push button 170 to urge the push button 170 away from the cam body 180. When the user desires to insert the pin 164 into the hole 166, the user pushes the push button 170 inward toward the tube holder 143 so that the push button 170 drives the cam body 180 distally until the proximal end of the cam surface 174 is moved distally beyond an adjacent edge of the first and second stop members 184a, 184b.

At this point, the interaction between the cam surfaces 172, 174 and the bias of the first spring 176 rotates the cam body 180 until the side of the cam surface 174 meets the side of the cam surface 172. When the push button 170 is released the second spring 177 pushes the push button 170 upward over the first stop member 184a that is configured to hold the cam body 180 in a position in which the pin 164 extends into the hole 166 in the tube holder 143 to lockingly engage the tubes 114. The same operation repeated will drive the pin 164 out of the hole 166 releasing the tube holder 143 for movement relative to the handle body 136 until the cam body slides proximally into engagement with the second stop member 184b that is configured to permit the cam body 180 to move further proximally until the pin 164 is moved out of engagement with the tubes 114.

Thus, when it is desired to finally deploy the clip 102, the user locks the position of the tubes 114 using the locking mechanism 162 and draws the control wires 116 proximally by moving the slider 146 proximally. This draws the clip 102 proximally and moves the tubes 114 distally into a space 127 within the connecting ring 120. As the tubes 114 move further into the connecting ring 120, the jaws 122 are pushed distally within the connecting ring 120 until a tab 123 formed at a proximal end of each of the jaws 122 moves distally until it reaches a slot 125. (See FIG. 14I).

Figure 14J:
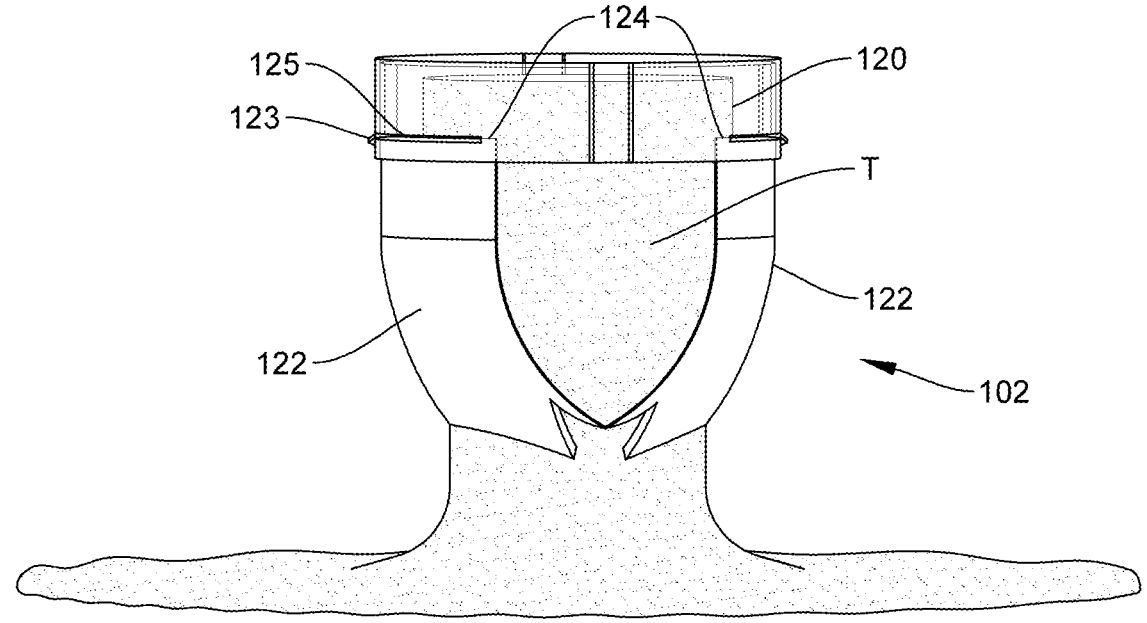
FIG. 14J shows the clip of FIG. 14I finally deployed clipped to the different portion of target tissue.

At this point, the tab 123 projects radially outward through the slot 125 under a natural bias of the tab 123 locking the clip 102 closed with the jaws 122 locked in position on the connecting ring 120. By moving the slider 146 further proximally after the jaws 122 have been locked relative to the connecting ring 120 and the control wires 116 have been placed in tension in this manner, the user will increase the tension on the control wires 116 by further movement of the slider 146 until a predetermined level of tension is reached. At this point, the frangible links 126 fail and the remaining portions 128 of the control wires 116 are separated from the enlarged distal ends 118 so that the clip 102 is completely separated from the rest of the system 100 and may be left in place clipped over the target tissue while the endoscope and the rest of the system 100 are removed from the body (FIG. 14J). Those skilled in the art will understand that any other known locking structure may be employed to lock the position of the jaws 122 relative to the connecting ring 120.

As shown in FIGS. 3, 9, 12 and 13, the clip 102 includes two jaws 122 which, in this embodiment are formed as two physically separate elements connected to one another via the connecting ring 120. The proximal end 124 of each jaw 122 is slidably received within a correspondingly sized space in the connecting ring 120 and each of the jaws 122 of this embodiment is formed of a sheet of metal (e.g., Nitinol) curved to match a curvature of the connecting ring 120 and, for example, heat treated to impart a bias to the jaws 122 toward the closed configuration.

The distal ends of the tubes 114 are, when advanced distally moved into contact with a proximal end of the connecting ring 120 so that further movement of the tubes 114 distally will move the connecting ring 120 and the rest of the clip 102 distally relative to the adapter 110. The control wires 116 extend distally into the space 127 within the connecting ring 120 and extend into the sockets 130 formed within the jaws 122 of the clip 102. Thus, movement of the control wires 116 distally relative to the tubes 114 pushes the jaws 122 distally within the space 127 in the connecting ring 120 as will be described in more detail below.

The jaws 122 of the clip 102 of this embodiment are held in the closed configuration by their natural bias. Each of the jaws 122 is formed to have a shape (e.g., when not subject to outside forces) that includes a proximal portion 150 (e.g., have a substantially cylindrical shape) with a distal portion 154 (e.g., having a curved shape) extending distally from each proximal portion 150 and curving toward a longitudinal axis L of the connecting ring 120. The jaws 122 are fixed to the connecting ring 120 so that the distal portions 154 extend toward one another to meet, for example, at the axis L.

A distal end 158 of each of the jaws 122 of this embodiment forms a plurality of tissue gripping teeth 160 that meet one another when the jaws 122 are closed. However, those skilled in the art will understand that these teeth 160 are optional and that, alternatively, the teeth 160 may be arranged so that the teeth 160 of a first one of the jaws 122 are offset from the teeth 160 of the other jaw 122 so that the teeth 160 interleave with one another when the jaws 122 are closed.

Figure 15:
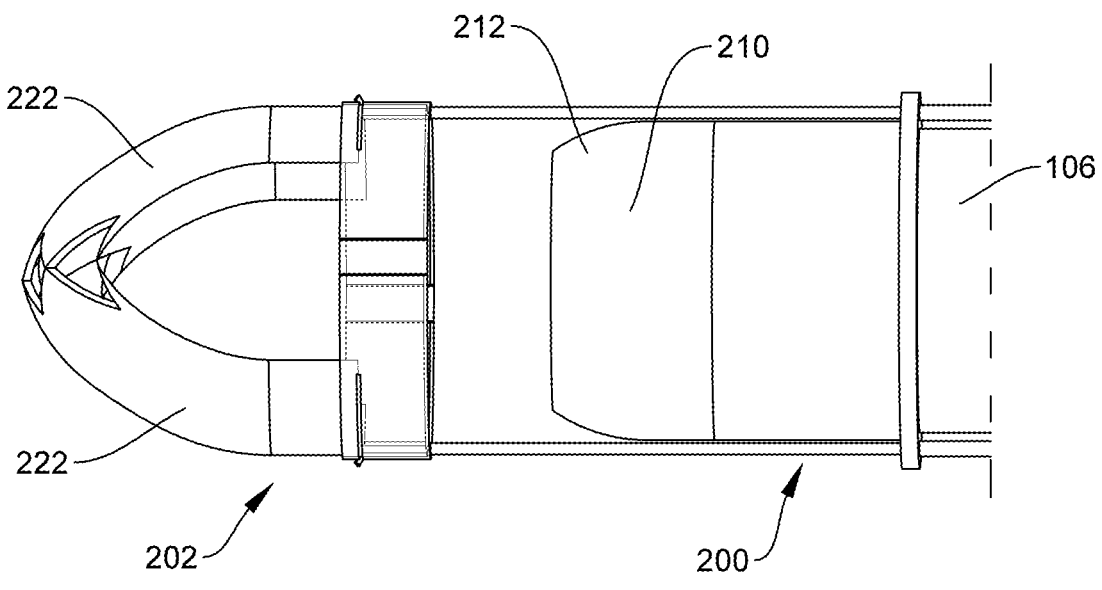
FIG. 15 shows a side view of a distal portion of a system according to an alternative embodiment with the clip in a review configuration wherein the system includes an adapter shaped to reduce a force required to re-open a clip.
Figure 16:
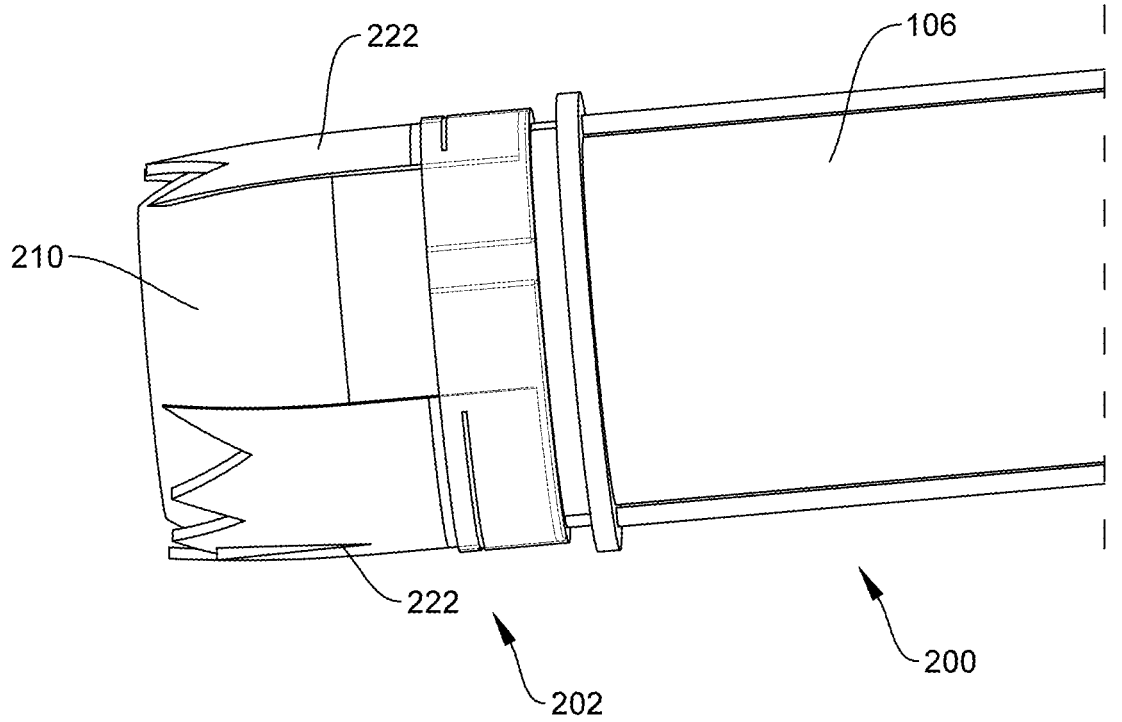
FIG. 16 shows a side view of the distal portion of the system of FIG. 15 with the clip retracted to an insertion configuration.

As shown in FIGS. 15 and 16, a system 200 according to a further embodiment of the invention is constructed and operates in a manner substantially identical to that of the system 100 except as described below. Specifically, the system 200 includes an adapter 210 that includes a curved distal end 212 that includes a curve substantially mirroring a curve of the interior surface of jaws 222 of a clip 202 that is constructed substantially similarly to the clip 102. The curved distal end 212 of the adapter 210 facilitates the re-opening of the clip 202 as it is drawn proximally back over the adapter 210 (e.g., when the user moves the clip from the review configuration back to the insertion configuration). As would be understood by those skilled in the art, the curved distal end 212 gradually engages the inner surfaces of the jaws 222 reducing the force required to force the jaws 222 to re-open in comparison to the system 100 and the adapter 110 that includes a blunt distal end.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
an adapter including a proximal portion configured to be mounted over a distal end of an insertion device and a distal portion extending distally from the proximal portion;
a clip configured to be mounted over the distal portion of the adapter, the clip including a connecting member connecting to first and second jaws configured to move between an insertion configuration, in which the first and second jaws extend about opposing portions of the distal portion of the adapter and are separated from one another to receive the tissue therebetween, and an initial deployed configuration, in which the clip is moved distally off of the adapter so that the first and second jaws are drawn toward one another to grip the tissue therebetween; and
a first extending member releasably coupled to the clip and movably connected to the adapter, the first extending member including a distal end extendable to abut against the connecting member; and
a first control wire slidably received within the first extending member so that movement of the first control wire relative to the first extending member moves the clip between the insertion configuration, the initial deployed configuration and a review configuration in which the adapter is withdrawn proximally away from the clip while the first control wire remains coupled to the clip to enhance visual observation of the clip, the first control wire being operable to retract the clip proximally over the adapter so that the clip is forced open as the clip is retracted over the adapter, a first releasable link connecting the first control wire to the clip, the first releasable link being configured to release when the first control wire is subject to a force exceeding a predetermined threshold value.

2. The system of claim 1, further comprising:
a second extending member releasably coupled to the clip and movably connected to the adapter, the second extending member including a distal end received within the connecting member; and a second control wire slidably received within the second extending member, the second control wire being operable in conjunction with the first control wire to retract the clip proximally over the adapter so that the clip is forced open as the clip is retracted over the adapter, a second releasable link connecting the second control wire to the clip, the second releasable link being configured to release when the second control wire is subject to a force exceeding the predetermined threshold value.

3. The system of claim 2, wherein the first control wire includes an enlarged distal end received within a first socket of the connecting member.

4. The system of claim 3, wherein the enlarged distal end of the first control wire is coupled to a proximal portion of the first control wire via a first link configured to separate when a force exerted on the first control wire exceeds a predetermined threshold level.

5. The system of claim 4, wherein the first socket is configured so that, when the first link separates, the enlarged distal end of the first control wire is retained within the first socket.

6. The system of claim 1, further comprising:

a first flexible member slidably receiving the first extending member therein, the first flexible member extending from a proximal end that, in use, remains outside a body accessible to a user, to a distal end coupled to the adapter.

7. The system of claim 6, wherein the first jaw includes a proximal end received within a first space in the connecting member, the first jaw including a substantially tubular proximal portion and a distal portion curving toward a distal end at a longitudinal axis of the connecting member.

8. The system of claim 7, wherein the second jaw includes a proximal end received within a second space in the connecting member, the second jaw including a substantially tubular proximal portion and a distal portion curving toward a distal end configured to meet the distal end of the first jaw at the longitudinal axis of the connecting member.

9. The system of claim 1, wherein the first jaw includes a tab at a proximal end thereof and wherein the connecting member includes a slot configured to receive the tab when the first jaw is moved distally through the connecting member to a locking position to lock the first jaw in position on the connecting member.

10. The system of claim 1, wherein the adapter includes a tapered distal end configured to slidably engage an inner surface of the first jaw as the first jaw is moved proximally over the adapter.

11. A clipping system for treating tissue, comprising:

an endoscope extending longitudinally from a proximal end to a distal end;

an adapter including a proximal portion configured to be mounted over a distal end of an insertion device and a distal portion extending distally from the proximal portion;

a clip configured to be mounted over the distal portion of the adapter, the clip including a connecting member connecting to first and second jaws configured to move between an insertion configuration, in which the first and second jaws extend about opposing portions of the distal portion of the adapter and are separated from one another to receive the tissue therebetween, and an initial deployed configuration, in which the clip is moved distally off of the adapter so that the first and second jaws are drawn toward one another to grip the tissue therebetween; and first and second extending members releasably coupled to the clip and movably connected to the adapter, each of the first and second extending members including a distal end abutting the connecting member; and first and second control wires each of which is slidably received within a corresponding one of the first and second extending members so that movement of the first and second control wires relative to the first and second extending members moves the clip between the insertion configuration, the initial deployed configuration and a review configuration in which the adapter is withdrawn proximally away from the clip while the first and second control wires remain coupled to the clip, the first and second control wires being operable to retract the clip proximally over the adapter so that the clip is forced open as the clip is retracted over the adapter, each of the first and second control wires being coupled to the connecting member via a releasable link configured to release when the first and second control wires are subject to a force exceeding a predetermined threshold value.

12. The system of claim 11, further comprising:

a handle;

a first actuator; and a locking mechanism selectively locking the first and second extending members to the first actuator.

13. The system of claim 12, wherein the first actuator is a spool slidable relative to a body of the handle and wherein the handle further includes a second actuator coupled to the first and second control wires, the second actuator configured to move the first and second control wires proximally and distally within the respective ones of the first and second extending members.

14. The system of claim 13, wherein the locking mechanism includes a spring biased member selectively lockable in a first position in which the spring biased member contacts the first and second extending members to lock the first and second extending members in position relative to the spool and a second position in which the spring biased member is out of contact with the first and second extending members freeing the first and second extending members to move relative to the spool.

15. The system of claim 12, wherein the adapter includes a tapered distal end configured to slidably engage an inner surface of the first jaw as the first jaw is moved proximally over the adapter.

* * * * *